(12) United States Patent
Knott

(10) Patent No.: US 6,670,506 B2
(45) Date of Patent: Dec. 30, 2003

(54) METHOD FOR PRODUCING DINITRO-DIAZA-ALKANES AND INTEREDIATE PRODUCTS THEREOF

(75) Inventor: Thomas Knott, Waldkraiburg (DE)

(73) Assignee: Nitrochemie Achau GmbH, Achau (DE)

( * ) Notice: Subject to any disclaimer, the term of this patent is extended or adjusted under 35 U.S.C. 154(b) by 148 days.

(21) Appl. No.: 09/959,631

(22) PCT Filed: Mar. 2, 2001

(86) PCT No.: PCT/EP01/02383

§ 371 (c)(1),
(2), (4) Date: Nov. 1, 2001

(87) PCT Pub. No.: WO01/64627

PCT Pub. Date: Sep. 7, 2001

(65) Prior Publication Data

US 2003/0041936 A1 Mar. 6, 2003

(30) Foreign Application Priority Data

Mar. 2, 2000  (DE) .......................................... 100 10 190

(51) Int. Cl.⁷ ............................................. C07C 241/00
(52) U.S. Cl. ...................... 564/109; 564/135; 564/141; 564/152; 568/944
(58) Field of Search ................. 564/109, 135, 564/141, 152; 568/944

(56) References Cited

U.S. PATENT DOCUMENTS 4,469,888 A  *  9/1984  Nauflett et al.
4,476,322 A  * 10/1984  Chang et al.

FOREIGN PATENT DOCUMENTS

| RU | 2148574 | * 5/2000 |
| RU | 2169140 | * 6/2001 |
| SU | 1616905 | * 12/1990 |

OTHER PUBLICATIONS

Tartakovsky, V.A et al Russian Chemical Bulletin (2000), 49(6) 1079–1081.*

* cited by examiner

Primary Examiner—Paul J. Killos
(74) Attorney, Agent, or Firm—Milton M. Field

(57) ABSTRACT

A method of synthesis of dinitro-diaza-alkanes and intermediate products thereto from alkylamines and esters, whereby a dialkyl ester of a dicarboxylic acid is reacted with an alkylamine in an aqueous medium to form the corresponding dialkyldiamide of the dicarboxylic acid;

the resulting dialkyldiamide is nitrated by means of conventional nitration agents to form the corresponding dialkyl-dinitroamide of the dicarboxylic acid and;

the resulting dialkyldinitroamide is reacted with methylamine and/or ethylamine in an aquous medium to yield a corresponding alkylnitroamine and the dimethyldiamide and/or diethyldiamide of the dicarboxylic acid, and the alkylnitroamine is isolated from that, and the isolated alkylnitroamine is condensed in a known manner to form the dinitro-diaza-alkanes.

13 Claims, No Drawings

METHOD FOR PRODUCING DINITRO-DIAZA-ALKANES AND INTEREDIATE PRODUCTS THEREOF

This application is a 371 of PCT/EP01/02383 Mar. 2, 2001.

BACKGROUND OF THE INVENTION

1. Field of the Invention

This invention relates to a method for producing dinitro-diaza-alkanes and intermediate products thereof.

2. Description of the Prior Art

For several years, there have been known propellant powders which contain dinitro-diaza-alkanes as an energetic plasticizer, also known as a blasting oil, specifically 2,4-dinitro-2,4-diaza-pentane in this case, either alone or in mixture with other suitable alkanes (U.S. Pat. Nos. 4,476,322, 4,457,791).

It is in the nature of dinitro-diaza-alkanes that the propellant powders produced with them have combustion characteristics which are almost independent of temperature. This is a highly desirable property, which means that the ambient temperature has little or no influence on the maximum gas pressure evolved in the system in combustion of the propellant charge. Accordingly, propellant powders having combustion properties that are independent of temperature make it possible to utilize the maximum potential power of the system over a wide temperature range.

Extensive use of dinitro-diaza-alkanes for production of propellant powders having a suitably balanced temperature characteristic has been prevented in the past by the fact that dinitro-diaza-alkanes are difficult to synthesize and thus are expensive.

In the case of a known production process (U.S. Pat. No. 4,476,322 with additional citations therein), 2,4-dinitro-2,4-diaza-pentane is synthesized from dimethylurea or diethylurea. The urea is nitrated with nitric acid, and the nitration product is hydrolyzed to methylnitroamine or ethylnitroamine. The resulting nitroamines are condensed to 2,4-dinitro-2,4-diaza-pentane with the help of paraformaldehyde and sulfuric acid. By a similar method, 2,4-dinitro-2,4-diaza-hexane and 3,5-dinitro-3,5-diaza-heptane as well as mixtures of the three alkanes mentioned here can also be produced (Tartakofsky et al., Russian Chemical Bulletin, 1993, 42, 1916 ff). Synthesis from urea gives only a relatively low total yield, and the diethylurea used in this synthesis is very expensive. In addition, the nitrated urea compound is an extremely unstable, temperature-sensitive and acid-sensitive explosive intermediate product.

In another proposed method for synthesis of the aforementioned mixture of three dinitro-diaza-alkanes, methylamine or ethylamine is reacted with a chloroformic acid ester using sodium hydroxide solution to form an intermediate product which is then nitrated with nitric acid. The nitration product is reacted by means of ammonia and ethanol at reflux to form methylnitroamine or ethylnitroamine, which is then condensed to form the dinitro-diaza-alkanes as in the preceding method. In this process, the next-to-last step in the synthesis of the nitroamines is very complicated and time-intensive, so that it cannot be implemented on a large scale industrially.

SUMMARY OF THE INVENTION

The object of this invention is to provide a method of synthesis of dinitro-diaza-alkanes which can be carried out easily and economically on a large scale industrially without any great safety risks.

This object is achieved according to this invention with the method characterized in a combination of the following steps:

1. reacting a diester of a dicarboxylic acid with an alkylamine in an aqueous medium to yield the corresponding dialkyldiamid of the dicarboxylic acid;
2. nitrating the resulting dialkyldiamide by means of the usual nitration agents to form the corresponding dialkyldinitroamide of dicarboxylic acid;
3. reacting the resulting dialkyldinitroamide to form the corresponding alkylnitroamine by mixing the dialkyldinitroamide in an aqueous medium with methylamine and/or ethylamine, separating the resulting dimethyldiamide and/or diethyldiamide of the dicarboxylic acid, acidifying the remaining product and then extracting the alkylnitroamine from that; and
4. condensing the isolated alkylnitroamine to form the dinitro-diaza-alkanes in the known manner.

The method is further characterized in the following embodiments:

a. the process starts with a dialkyl ester of an aliphatic dicarboxylic acid, preferably oxalic acid;
b. the process starts with oxalic acid diethyl ester;
c. methylamine and/or ethylamine, preferably ethylamine, is used in the first step;
d. methylamine is used in the third step;
e. in the first step, the alkylamine in an aqueous solution is added gradually to the dialkyl ester at a temperature between 0° C. and 80° C. and the reaction product is filtered out after a secondary reaction time of 0.5 to 3 hours, preferably one to two hours;
f. in the second step lactic acid, nitric acid, acetic anhydride or dinitrogen pentoxide with or without a solvent is used as the nitration agent;
g. the dialkyldiamide is dissolved in nitric acid, and mixed with concentrated sulfuric acid at a temperature below 20° C., then the reaction product is poured onto ice and then filtered or separated;
h. in the third step the remaining product is acidified with concentrated sulfuric acid, and then the alkylnitroamine is extracted with an organic solvent preferably with ether;
i. the fourth step begins with paraformaldehyde in the concentrated sulfuric acid to which alkylnitroamine is added gradually at a temperature between −20° C. and +20° C., then diluting with water and extracting with an organic solvent and finally washing the organic phases and removing the solvent;
j. the dimethyldiamide and/or diethyldiamide which is separated as a by-product in the third step is nitrated again in the second step and used in the third step to synthesize methylnitroamine and ethylnitroamine; and
k. in the second step dimethyldiamide and diethyldiamide are nitrated together, and the two reaction products are jointly reacted to form methylnitroamine and ethylnitroamine in the third step.

The invention is more broadly concerned with a method of synthesis of alkylnitroamines from alkylamines and esters, characterized by the following steps:

1. reacting a diester of a dicarboxylic acid with an alkylamine in an aqueous medium to yield the corresponding dialkyldiamide of the dicarboxylic acid;
2. nitrating the resulting dialkyldiamide by means of the usual nitration agents to form the corresponding dialkyldinitroamide of dicarboxylic acid; and
3. reacting the resulting dialkyldinitroamide to form the corresponding alkylnitroamine by mixing the dialkyldinitroamide in an aqueous medium with methylamine and/or ethylamine, separating the resulting dimethyldiamide and/or diethyldiamide of the dicarboxylic acid, acidifying the remaining product and then extracting the alkylnitroamine from that.

DETAILED DESCRIPTION OF THE INVENTION

The method according to this invention begins with a dialkyl ester of a dicarboxylic acid, preferably oxalic acid diethyl ester, which is reacted with a primary aliphatic amine, preferably ethylamine, to yield the corresponding dialkyldiamide. The reaction takes places in an aqueous medium. The reaction temperature is between 0 and 80° C. The dialkyldiamides are obtained in the form of a precipitate which can be filtered out. The following formula describes the first step of the process according to this invention:

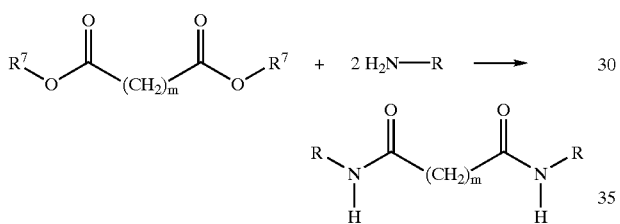

$R=C_nH_{2n+1}$ with $n=1, 2, \ldots, 10$ $m=0, 1, \ldots, 10$

This formula represents the case when a dialkyldiamide of the dicarboxylic acid is formed with a primary aliphatic amine. Instead of diamides with aliphatic groups, however, diamides of the dicarboxylic acid may be formed with cyclic or aromatic groups, this process being controlled through the choice of a suitable cyclic or aromatic amine.

In the second step of the method according to this invention, the resulting dialkyldiamides are nitrated by means of conventional nitration agents to yield the corresponding dialkyldinitroamides. This is shown by the following formula:

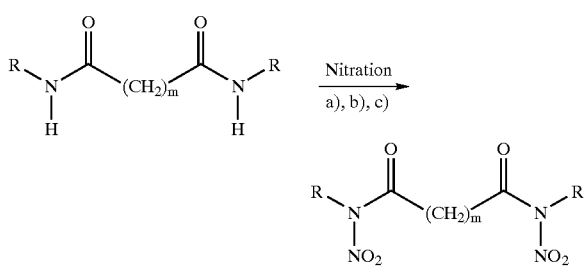

a) $HNO_3/H_2SO_4$
b) $HNO_3$/acetic anhydride
c) $N_2O_5$ $R=C_nH_{2n+1}$ with $n=1, 2, \ldots, 10$ $m=0, 1, \ldots, 10$ If the second step begins with diamides which have cyclic or aromatic groups, the result is dinitroamide compounds having the corresponding groups. Nitration takes place with the help of the usual nitration agents, preferably with the help of lactic acids, nitric acid, acetic anhydride or nitrogen pentoxide, with or without a solvent. The temperature during the addition of the nitration agent should be in the range of −20° C. to +20° C. In the case of the liquid dinitro compounds, two phases are formed and the solid dinitro compounds can be filtered out.

In another step, namely the third step, the dialkyldinitroamides are reacted with methylamine and/or ethylamine, forming dimethyldiamides and/or diethyldiamides as by-products, which can in turn be used after nitration to synthesize methylnitroamine and ethylnitroamine, and they can be used after acidification to produce alkylnitroamines in which the alkyl group corresponds to that of the dinitroamide. The third step is represented by the following formula:

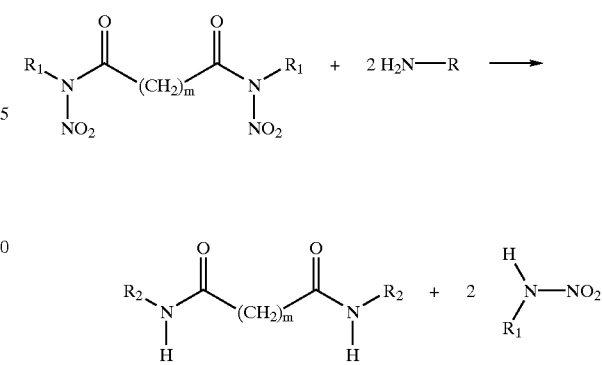

$R_1=C_nH_{2n+1}$ with $n=1, 2, \ldots, 10$ $m=0, 1, \ldots, 10$ $R_2$=methyl, ethyl The alkylnitroamines are preferably isolated by extraction with the help of an organic solvent such as diethyl ether, dichloromethane, methyl-tert-butyl ether (MTBE), ethyl acetate or toluene, but ether is preferred.

In the forth step, the alkylnitroamines thus isolated are condensed to form the dinitro-diaza-alkanes in a known manner. Suitable methods for this are disclosed in the U.S. Pat. No. 4,476,322 and in the article by Tartakofsky et al. (loc. cit.). A preferred method of condensation can be taken from claim 10, using a 50% to 98% sulfuric acid. The solvent used here may be the same as that which was also used in the third step and is used further here without being removed at the end. Schematically, the following formula represents the fourth step:

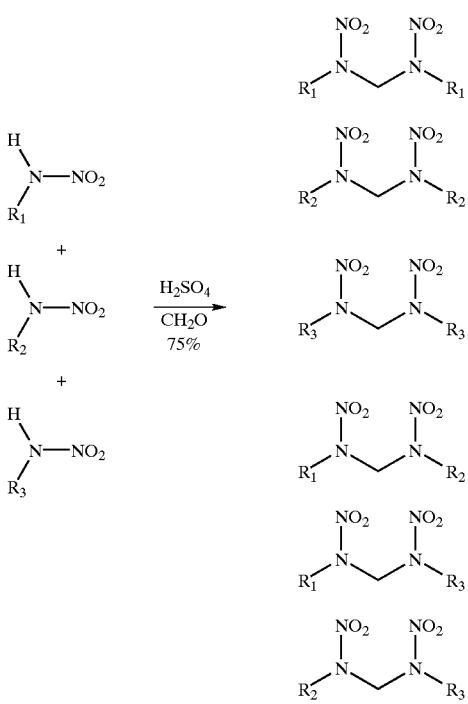

$R_1$, $R_2$, $R_3 = C_nH_{2n+1}$ with n=1, 2, ..., 10

This invention is directed in particular at the synthesis of a mixture of the three compounds 2,4-dinitro-2,4-diaza-pentane, 2,4-dinitro-2,4-diaza-hexane and 3,5-dinitro-3,5-diaza-heptane, as mentioned above and referred to here as DNDA 57, because this mixture seems to be especially suitable for producing propellant powders having a balanced temperature characteristic. The desired composition of the mixture can be controlled in condensation through the relative amounts of the different nitroamines used.

In this connection, a refinement of this invention is especially advantageous. In this case, methylnitroamine and ethylnitroamine are synthesized together in the same process, and their ratio can then be adjusted from the beginning according to the desired composition of the DNDA 57, so that the two nitroamines can be condensed immediately without further workup to form DNDA 57 in the fourth synthesis step.

In comparison with the synthesis pathways discussed in the introduction, the method according to this invention offers several advantages. The cost of the starting materials is low and the starting materials are available in large quantities. The yields are relatively high and the intermediate products obtained can be isolated. This process can be implemented on an industrial scale comparatively easily. Finally, it can be carried out in an environmentally acceptable manner, because a large portion of the reactions take place in an aqueous medium, and all the waste products are highly biodegradable.

Furthermore, this invention concerns, as novel substances, dialkyldinitroamides of a higher dicarboxylic acid as well as dinitroamides of a dicarboxylic acid in which the alkyl group is replaced by a cyclic group or an aromatic group. Such substances are obtained as intermediate products when the process according to this invention is carried out, namely at the end of the second step, i.e., by nitration, where the group is controlled through an appropriate choice of amine used in the first step. The preferred use of these novel substances, namely the dialkyl-dinitroamides, is their use as intermediate products for synthesis of alkyl-nitroamines or dinitro-diaza-alkanes, e.g., with the help of step 3 or steps 3 and 4 of the process according to this invention. The dimethyldinitroamide of oxalic acid is already known from Chemical Abstracts, reference 46: 904G, but there is no mention of this application there.

This invention is explained below with additional details, namely on the basis of examples for the synthesis of methylnitroamine and ethylnitroamine and for the synthesis of the resulting energetic plasticizer mixture DNDA 57.

1) Synthesis of N,N'-dimethyloxalic acid diamide from oxalic acid diethyl ester and methylamine

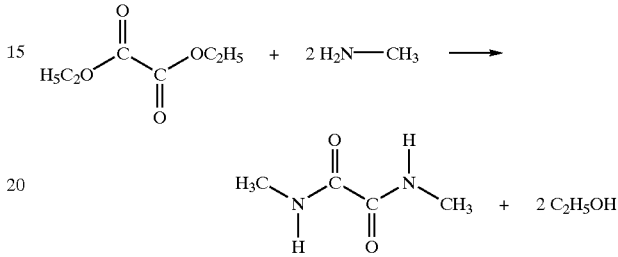

While stirring, 389 g (5.0 mol, d=0.90, 432 ml) 40% methylamine solution is added by drops to 292 g (2.0 mol, d=1.08, 270 ml) oxalic acid diethyl ester. The temperature should not exceed 80° C. After one hour of a secondary reaction time, the colorless solid is filtered out, washed with a small amount of water and dried. Yield: 125 g (1.1 mol, 54%).

2) Synthesis of N,N'-diethyloxalic acid diamide from oxalic acid diethyl ester and ethylamine

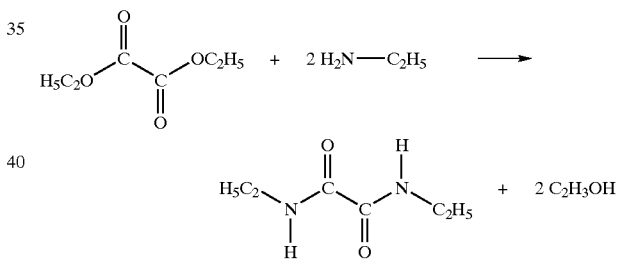

While stirring, 387 g (5.0 mol, d=0.81) 70% ethylamine solution is added by drops to 292 g (2.0 mol, d=1.08) oxalic acid diethyl ester. After this dropwise addition, the mixture is stirred for one hour at room temperature. The colorless solid is filtered out, washed with a small amount of water and dried. Yield: 154 g (1.1 mol, 53%).

3) Synthesis of oxalic acid bis-[methylnitroamide]:

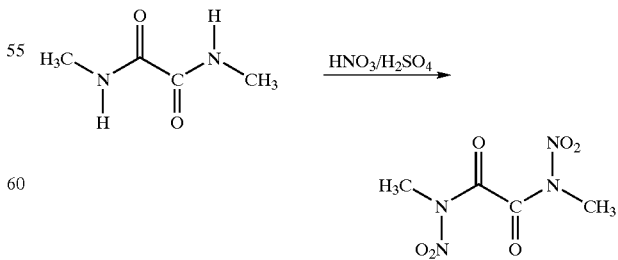

10.0 g (0.09 mol) oxalic acid-bis-[methylamide] is dissolved in 25 ml 96% $HNO_3$ and mixed with 50 ml $H_2SO_4$ while preventing excessive heating (25° C. to 45° C.). The resulting paste is poured onto ice, filtered, washed with water until neutral and dried. Yield: 14.8 g (0.07 mol, 79%), m.p 124° C. from ethanol.

4) Synthesis of oxalic acid bis-[ethylnitroamide]:

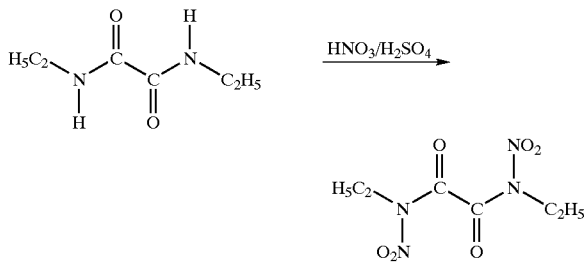

26.0 g (0.18 mol) oxalic acid bis-[ethylamide] is dissolved in 50 ml 96% $HNO_3$ and mixed with 100 ml $H_2SO_4$ while preventing excessive heating (25° C. to 45° C.). Two phases are formed. The organic phase is separated, then washed with water and saturated with sodium carbonate solution. Yield: 30.6 g (0.13 mol, 89%).

5) Synthesis of methylnitroamine:

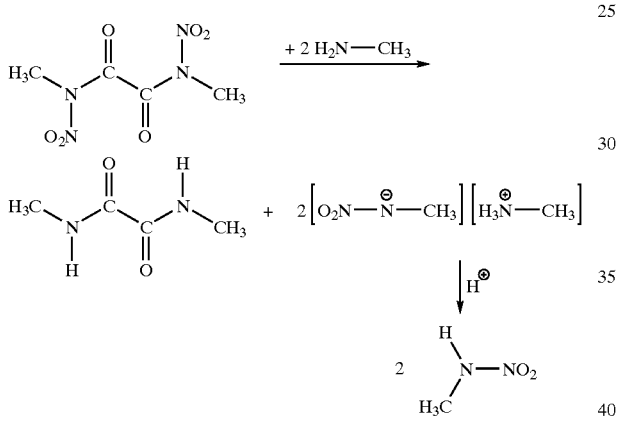

10.0 g (0.05 mol) oxalic acid bis-[methylnitroamide] is mixed in small portions with 17.5 ml (0.23 mol) 40% methylamine solution. The mixture heats up and changes gradually. After approximately one hour, the mixture is filtered to remove the oxalic acid bis-[methylamide] that is formed again and then it is washed with a small amount of water. The aqueous phase is acidified with $H_2SO_4$, forming methylnitroamine and methylamine sulfate. Then extraction is performed three times with 50 ml ether each time. After drying over $MgSO_4$, the ether is removed. Yield: 6.2 g (0.08 mol, 82%).

6) Synthesis of ethylnitroamine:

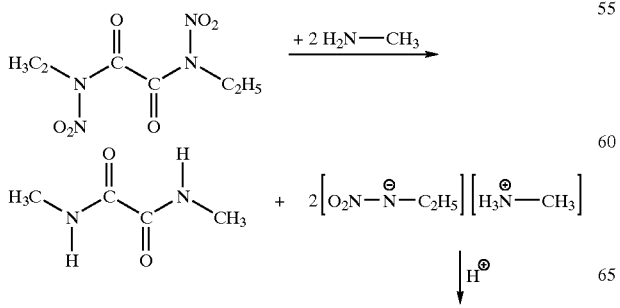

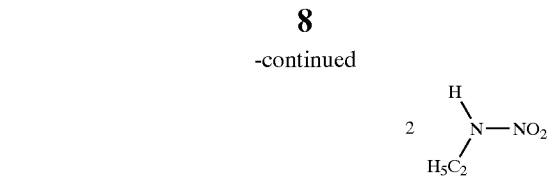

11.7 g (0.05 mol) oxalic acid bis-[ethylnitroamide] is mixed in small portions with 17.5 ml (0.23 mol) 40% methylamine solution. The mixture heats up and changes gradually. After approximately one hour, the oxalic acid bis-[methylamide] that has formed again is filtered out and washed with a small amount of water. The aqueous phase is acidified with $H_2SO_4$, forming ethylnitroamine and methylamine sulfate. Then extraction is performed three times with 50 ml ether each time. After drying over $MgSO_4$, the ether is removed. Yield: 8.9 g (0.10 mol, 99%).

7) Reaction of a mixture of methylnitroamine and ethylnitroamine to form DNDA 57

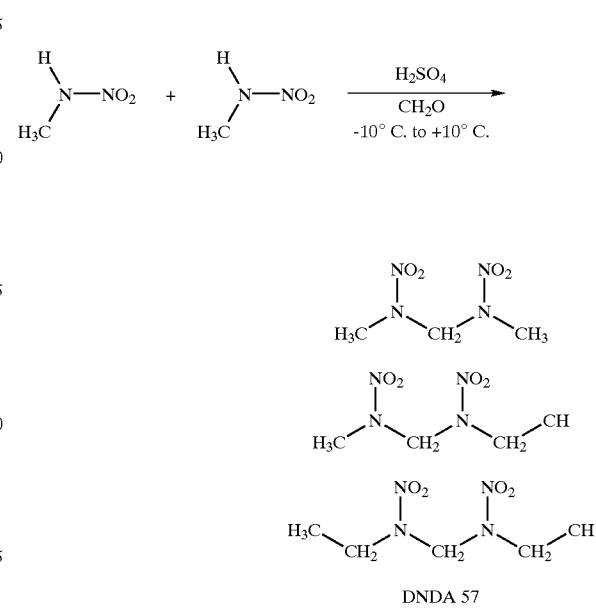

To synthesize DNDA 57, 2.3 g paraformaldehyde is placed in 40 ml 75% sulfuric acid and cooled to 0° C. A mixture of 7.2 g (95 mmol) methylnitroamine and 4.5 g (50 mmol) ethylnitroamine is added by drops in such a way that the temperature of the reaction solution does not rise above 5° C. After a secondary reaction time of one hour, the mixture is poured into ice water, and the aqueous phase is extracted with a total of approximately 50 ml dichloromethane. The combined organic phases are washed with saturated sodium carbonate solution and dried over magnesium sulfate. After removing the solvent, this yields DNDA 57 in a yield of 10.3 g (83%). The ratio of the three components is as follows:

2,4-Dinitro-2,4-diaza-pentane approximately 45%

2,4-Dinitro-2,4-diaza-hexane approximately 44%

3,5-Dinitro-3,5-diaza-heptane approximately 11%

OVERVIEW OF DNDA SYNTHESIS

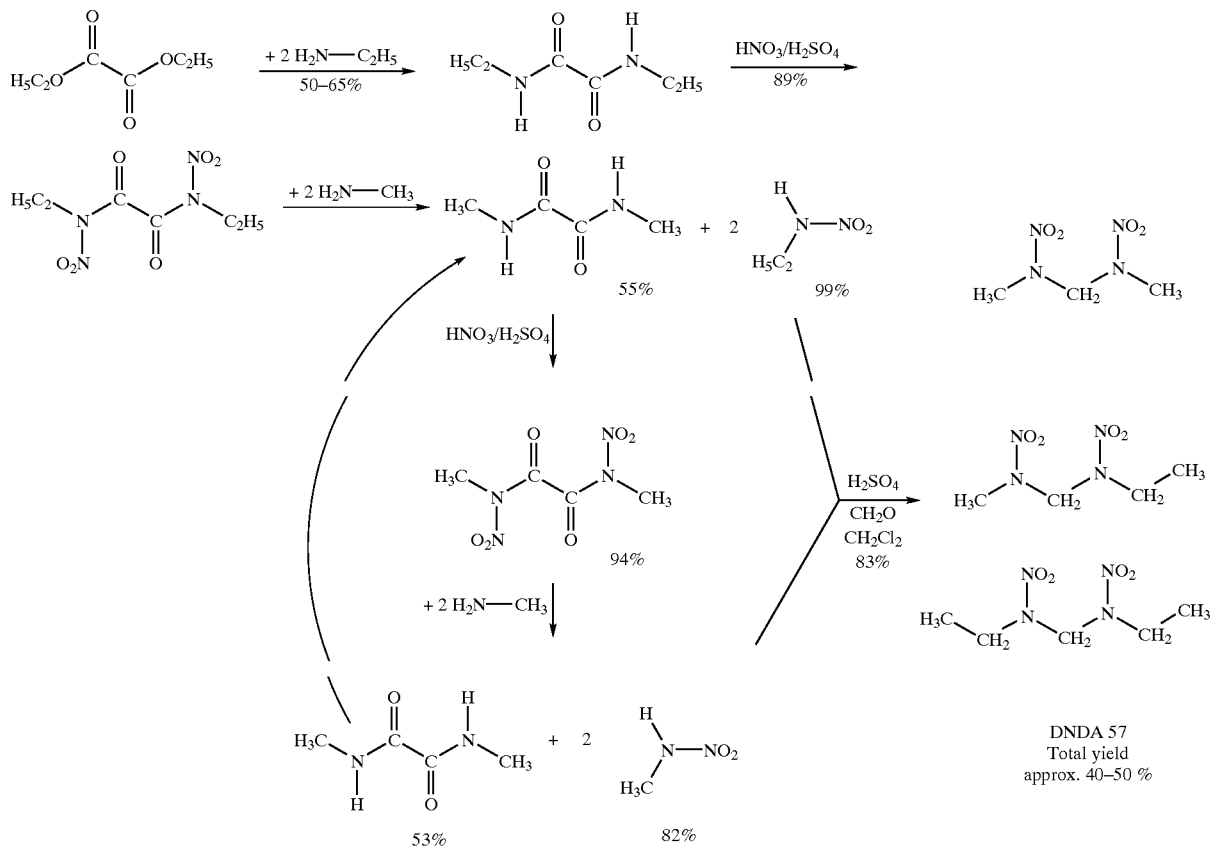

The preceding overview of DNDA synthesis shows how the individual steps described above are combined to form a self-contained method of synthesis of DNDA 57. Starting with oxalic acid diethyl ester and ethylamine, diethyloxalic acid diamide is synthesized first, and then by nitration with the help of nitric acid and sulfuric acid, oxalic acid diethyldinitroamide is obtained from it.

The latter is reacted with methylamine to form dimethyloxalic acid diamide as a by-product and ethyl nitroamine. The by-product is nitrated as before, yielding oxalic acid dimethyldinitroamide. By reacting this intermediate product with methylamine, this again yields dimethyloxalic acid diamide as a by-product, which is again sent for nitration, and also yields methylnitroamine. The two resulting nitroamines are converted together to the desired DNDA 57 mixture of three nitro-diaza-alkanes by joint condensation with the help of sulfuric acid and paraformaldehyde. In the overview, the yields obtained in the individual steps are given. The total yield is approximately 40 to 50%.

One variant of synthesis methods 3) through 6) above is simultaneous synthesis of methylnitroamine and ethylnitroamine from the two dialkyloxalic acid diamides:

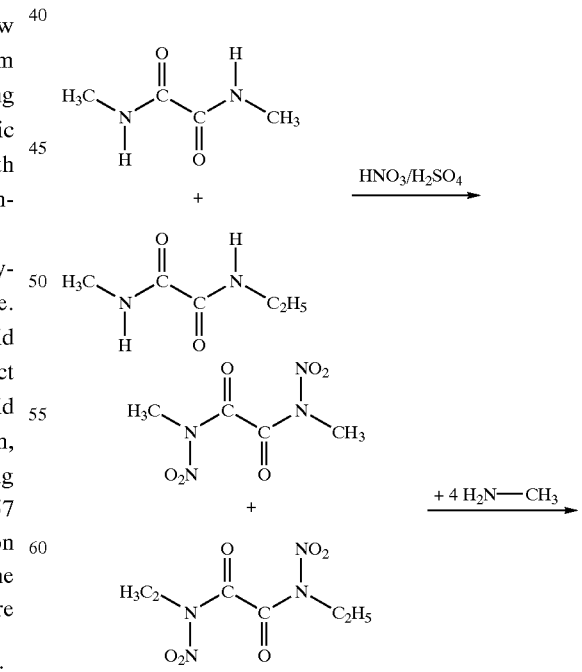

-continued

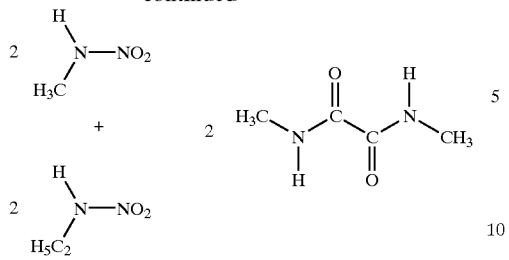

15.2 g (0.13 mol) oxalic acid bis-[methylamide] and 6.5 g (0.04 mol) oxalic acid bis-[ethylamide] are dissolved in 50 ml 96% $HNO_3$ and mixed with 100 ml $H_2SO_4$ while preventing excessive heating (25 to 45° C.). The resulting paste is poured onto ice, filtered and washed with water until neutral. The resulting oxalic acid diamides are mixed in small portions with a total of approximately 60 ml (0.79 mol) 40% methylamine. The mixture heats up and changes gradually. After approximately one hour, the oxalic acid bis-[methylamide] which is formed again is filtered out and washed with a small amount of water. The aqueous phase is acidified with $H_2SO_4$, forming methylnitroamine, ethylnitroamine and methylamine sulfate. Then extraction is performed three times with 50 ml ether each time. After drying over $MgSO_4$, the ether is removed. The two nitroamines are obtained in the desired ratio in a yield of 61% and can be used immediately in the next synthesis step without any further work-up.

What is claimed is:

1. A method of synthesis of dinitro-diaza-alkanes from alkylamines and esters, characterized by a combination of the following steps:

1. reacting a diester of a dicarboxylic acid with an alkylamine in an aqueous medium to yield the corresponding dialkyldiamide of the dicarboxylic acid;
   2. nitrating the resulting dialkyldiamide by means of the usual nitration agents to form the corresponding dialkyldinitroamide of dicarboxylic acid;
   3. reacting the resulting dialkyldinitroamide to form the corresponding alkylnitroamine by mixing the dialkyldinitroamide in an aqueous medium with methylamine and/or ethylamine, separating the resulting dimethyldiamide and/or diethyldiamide of the dicarboxylic acid, acidifying the remaining product and then extracting the alkylnitroamine from that; and
   4. condensing the isolated alkylnitroamine to form the dinitro-diaza-alkanes in the known manner.

2. A method according to claim 1, whereby the process starts with a dialkyl ester of an aliphatic dicarboxylic acid.

3. A method according to claim 2, whereby the process starts with oxalic acid diethyl ester.

4. A method according to claim 1, whereby methylamine and/or ethylamine is used in the first step.

5. A method according to claim 1, whereby methylamine is used in the third step.

6. A method according to claim 2, whereby in the first step, the alkylamine in an aqueous solution is added gradually to the dialkyl ester at a temperature between 0° C. and 80° C., and the reaction product is filtered out after a secondary reaction time of 0.5 to 3 hours.

7. A method according to claim 1, whereby in the second step lactic acid, nitric acid, acetic anhydride or dinitrogen pentoxide with or without a solvent is used as the nitration agent.

8. A method according to claim 7, whereby the dialkyldiamide is dissolved in nitric acid, and mixed with concentrated sulfuric acid at a temperature below 20° C., then the reaction product is poured onto ice and then filtered or separated.

9. A method according to claim 1, whereby in the third step the remaining product is acidified with concentrated sulfuric acid, and then the alkylnitroamine is extracted with an organic solvent.

10. A method according to claim 1, whereby the fourth step begins with paraformaldehyde in the concentrated sulfuric acid to which alkylnitroamine is added gradually at a temperature between −20° C. and +20° C., then diluting with water and extracting with an organic solvent and finally washing the organic phases and removing the solvent.

11. A method according to claim 1, whereby the dimethyldiamide and/or diethyldiamide which is separated as a by-product in the third step is nitrated again in the second step and used in the third step to synthesize methylnitroamine and ethylnitroamine.

12. A method according to claim 4, whereby in the second step dimethyldiamide and diethyldiamide are nitrated together, and the two reaction products are jointly reacted to form methylnitroamine and ethylnitroamine in the third step.

13. A method of synthesis of alkylnitroamines from alkylamines and esters, characterized by the following steps:

1. reacting a diester of a dicarboxylic acid with an alkylamine in an aqueous medium to yield the corresponding dialkyldiamide of the dicarboxylic acid;
   2. nitrating the resulting dialkyldiamide by means of the usual nitration agents to form the corresponding dialkyldinitroamide of dicarboxylic acid; and
   3. reacting the resulting dialkyldinitroamide to form the corresponding alkylnitroamine by mixing the dialkyldinitroamide in an aqueous medium with methylamine and/or ethylamine, separating the resulting dimethyldiamide and/or diethyldiamide of the dicarboxylic acid, acidifying the remaining product and then extracting the remaining product and then extracting the alkylnitroamine from that.

* * * * *